United States Patent [19]

Šorm et al.

[11] 4,005,150

[45] Jan. 25, 1977

[54] PHENYL ETHERS HAVING JUVENILE HORMONE ACTIVITY

[75] Inventors: Frantisek Šorm; Miroslav Svoboda; Jiři Zavada; Karel Slama; Zdeněk Arnold, all of Prague, Czechoslovakia

[73] Assignee: Ceskoslovenska akademie ved, Prague, Czechoslovakia

[22] Filed: May 18, 1971

[21] Appl. No.: 144,631

[30] Foreign Application Priority Data

May 22, 1970 Czechoslovakia ............... 3600-70
Nov. 27, 1970 Czechoslovakia ............... 8032-70

[52] U.S. Cl. .................. 260/613 D; 260/613 R; 260/607 A; 260/609 E; 260/609 F; 424/337; 424/341

[51] Int. Cl.² ...................................... C07C 43/20

[58] Field of Search ....... 260/613 D, 613 R, 612 D, 260/614 R; 424/34.1

[56] References Cited

OTHER PUBLICATIONS

Slama et al., *Proceedings of the National Academy of Sciences*, vol. 54, (1965), pp. 411–414.
Borkovec, *Insect Chemosterilants*, (1966), pp. 61–63.
Bowers, *Science*, vol. 164, (1969), pp. 323–325.

*Primary Examiner*—Bernard Helfin
*Attorney, Agent, or Firm*—Beveridge, DeGrandi, Kline

[57] ABSTRACT

Novel nitrophenyl and halophenyl compounds having a side chain substituted with hydroxy or ether radical useful for insect control.

13 Claims, No Drawings

PHENYL ETHERS HAVING JUVENILE HORMONE ACTIVITY

The present invention relates to novel compounds possessing insect juvenile hormone activity according to the general formula I and II:

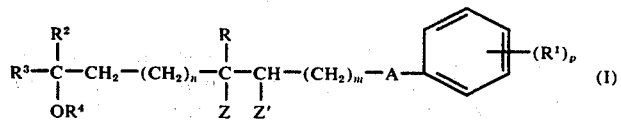
(I)

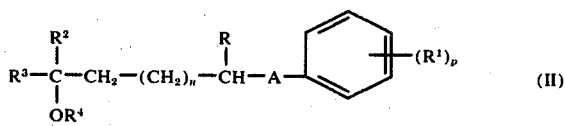
(II)

wherein, A is oxygen, sulfur, sulfinyl or sulfonyl; $R^1$ is nitro or halo; each of R, $R^2$ and $R^3$ is lower alkyl; $R^4$ is hydrogen, lower alkyl, cycloalkyl or aralkyl; m is the positive integer one or two; n is the positive integer two or three; p is zero or the positive integer one to five; each of Z and Z' is hydrogen or together form a carbon-carbon bond.

The term lower alkyl, as used herein, refers to an alkyl group, straight or branched, having a chain length of one to six carbon atoms. The term aralkyl, as used herein, refers to aralkyl or seven to twelve carbon atoms, such as benzyl, phenethyl, methylbenzyl and naphthylmethyl. The term cycloalkyl, as used herein, refers to cycloalkyl group of four to eight carbon atoms. The term halo refers to bromo, chloro, fluoro and iodo.

The novel compounds of formulas I and II are useful for the control of insects. The utility of these compounds as insect control agents is believed to be attributable to their juvenile hormone activity. They are preferably applied to the immature insect, namely — during the embryo, larvae or pupae stage in view of their ability to inhibit metamorphosis and otherwise cause abnormal development. These compounds are effective control agents for Hemipteran, such as Lygaeidae, Miridae and Pyrrhocoridae; Coleopteran, such as Tenebrionidae; Lepidopteran, such as Pyralidae, Noctiidae and Gelechiidae; Dipteran, such as mosquitoes; Orthoptera, such as roaches; and Homoptera, such as aphids. The compounds can be applied at low dosage levels of the order of 0.001 μg. to 25 μg. per insect. Suitable carrier substances include liquid or solid carriers, such as water, mineral or vegetable oils, talc, silica and natural or synthetic resin. The control of insects in accordance with the present invention is accomplished by spraying, dusting or exposing the insects to the vapor of the novel compounds. Generally, a concentration of less than 50% of the active compound is employed. The formulation can include insect attractants, emulsifying agents and wetting agents to assist in the application and efficiency of the active ingredient.

In the description following, each of A, R, $R^1$, $R^2$, $R^3$, m, n and p is as defined above.

The compounds of formulas I and II are prepared from the precursors of formulas III and IV (A' is oxygen or sulfur):

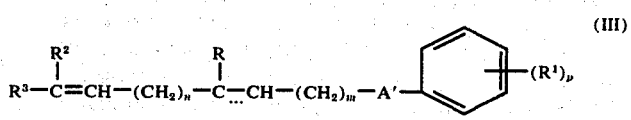
(III)

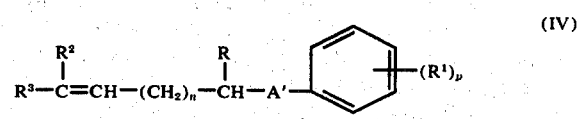
(IV)

by the addition of water or an alcohol ($R^4$—OH). The addition of water or an alcohol to the terminal double bond of III or IV may be performed in the presence of acid catalyst or, preferably, by a selective method reported by B. C. Brown and Min-Hon Rei, J. Amer. Chem. Soc. 91, 5646 (1969). This method consists in the reaction of an unsaturated compound with water or the appropriate alcohol and a mercuric salt and, without isolating the mercury-containing intermediate, subsequent reduction. Suitable mercuric salts include mercuric acetate and other acylates, mercuric nitrate, mercuric trifluoroacetate and mercuric halides. Suitable reducing agents include the alkali metal borohydrides, hydrazine and sodium amalgam.

The precursors III and IV can be prepared by the alkylation of a phenol V or thiophenol VI with a halide of formula VII or VIII. The broken line indicates the presence or absence of a carbon-carbon bond and X is bromo or chloro.

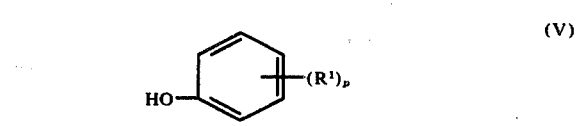
(V)

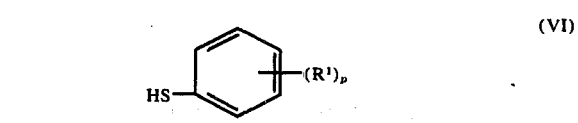
(VI)

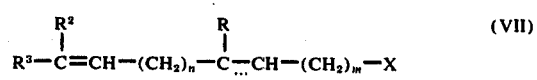
(VII)

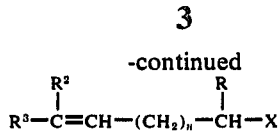

(VIII)

The alkylation is conducted in an organic solvent inert to the reaction in the presence of a base.

The compounds I and II can be prepared also by the reaction of a phenol or thiophenol of formula V or VI with the alkylating agent IX or X wherein $R^{4'}$ is lower alkyl or aralkyl:

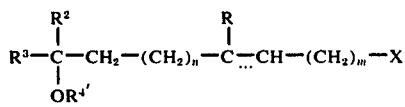

(IX)

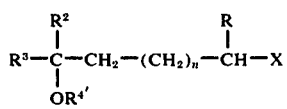

(X)

The sulfinyl compounds of the present invention are prepared by treatment of a thioether with sodium metaperiodate, hydrogen peroxide, or the like, at a temperature of from about 0° to 20° C for about 1 to 6 hours. The reaction usually affords some of the sulfonyl compound also which can be separated by chromatography. By using more than one mole of sodium periodate or hydrogen peroxide, higher temperature and longer reaction time, the reaction favors formation of the sulfonyl compounds. Preparation of sulfinyl and sulfonyl compounds is described by N. J. Leonard et al., *Journal of Organic Chemistry* 27, 282 (1962).

The bromide and chloride of formula VII can be prepared from the corresponding C-1 alcohol which is obtained by the reduction of an acid or ester of the formula:

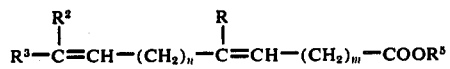

(XIII)

in which $R^5$ is hydrogen or lower alkyl, using lithium aluminum hydride, or the like. The overall synthesis can be outlined as follows:

In the practice of the above process, a dialkyl ketone of formula XI is reacted with a Wittig reagent of formula XI' (⅙ is phenyl):

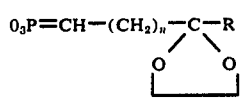

(XI')

to form the ethylene ketal of a compound of formula XII which is hydrolyzed by treatment with acid to the ketone XII. The ketone XII is then reacted with the carbanion of dialkyl carbalkoxyphosphonate to yield the α,β-unsaturated ester XIII (m is zero and $R^5$ is lower alkyl) or with β-carboxyethyltriphenylphosphonium chloride in the presence of base to yield the β,γ-unsaturated acid (XIII; m is one and $R^5$ is hydrogen). Suitable conditions are described by H. S. Corey et al., *J. Am. Chem. Soc.* 86, 1884–1885 (1964), the disclosure of which is incorporated by reference. The acid or ester XIII is then reduced by conventional techniques using lithium aluminum hydride or like reducing agent to yield the primary alcohol XIV which is converted to the C-1 bromide or chloride VII using phosphorus trichloride, phosphorus tribromide, phosphorus pentachloride, phosphorus pentabromide, or the like. Compounds of formula VII can be prepared also using the synthesis of Bowers, Science 164, 323–325 (1969) which is incorporated by reference. The compounds of formula XII' are prepared by reduction of the ketone XII using sodium borohydride, lithium aluminum hydride, or the like, and the conversion of the secondary alcohol XII' into the bromide or chloride VIII using phosphorus tribromide or phosphorus trichloride.

The following examples are provided to illustrate the practice of the present invention and the preparation of the novel compounds. Temperature is given in degrees centigrade.

EXAMPLE 1

(A) To a solution of p-nitrophenol (2 g.) in dimethylformamide (10 ml.) is added anhydrous potassium carbonate (2 g.) and 3,7-dimethylocta-2,6-dienyl bromide (3.1 g.). The reaction is kept at 50° for 12 hours, diluted with water and extracted with ether. The ethereal extract is washed with 5% aqueous sodium hydrox-

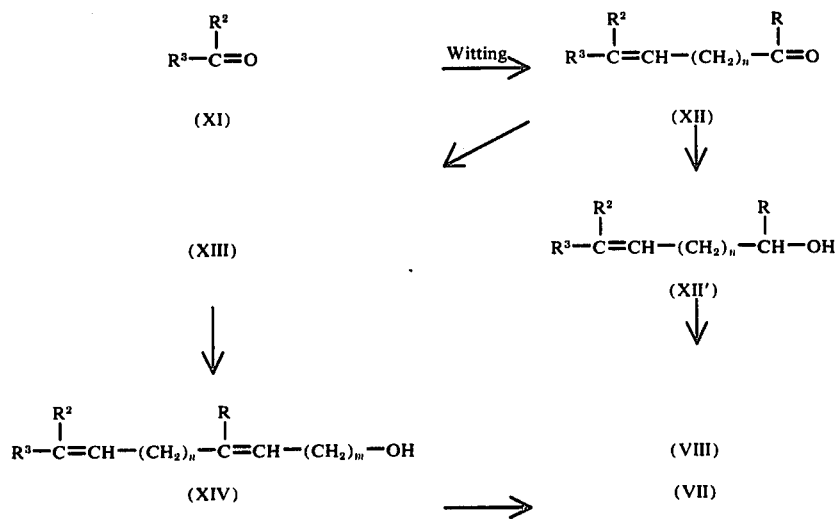

ide and dried over sodium sulfate. The crude product is purified by distillation to yield 3,7-dimethylocta-2,6-dienyl p-nitrophenyl ether.

By use of the above procedure, p-nitrophenol is alkylated using 3,7-dimethyloct-6-enyl bromide, 1,5-dimethylhex-4-enyl bromide, 3,7-dimethylnona-2,6-dienyl bromide, 3-ethyl-7-methylnona-2,6-dienyl bromide and 4,8-dimethylnona-3,7-dienyl bromide to yield the p-nitrophenyl ethers under Column I:

I 3,7-dimethyloct-6-enyl p-nitrophenyl ether,
1,5-dimethylhex-4-enyl p-nitrophenyl ether,
3,7-dimethylnona-2,6-dienyl p-nitrophenyl ether,
3-ethyl-7-methylnona-2,6-dienyl p-nitrophenyl ether,
4,8-dimethylnona-3,7-dienyl p-nitrophenyl ether.

(B) A solution of mercuric acetate (1.6 g.) in water (5 ml.) is diluted with tetrahydrofuran (15 ml.) and the resulting yellowish suspension treated dropwise with p-nitrophenyl geranyl ether (1.39 g.). The reaction mixture which becomes homogeneous in a short period of time, is stirred for additional 10 minutes, cooled with ice and water and treated with aqueous 3M—NaOH (5 ml.) and a solution of sodium borohydride (0.1g) in 3M—NaOH (5 ml.). After 15 minutes, the reaction mixture is diluted with water and extracted with petroleum ether. The ether is washed with water and evaporated to yield 1 g. of a crude product containing 50% of the required product which is obtained in the pure state by chromatography on silica gel (with the use of benzene + 5% of acetone as eluting agent) to yield 7-hydroxy-3,7-dimethyloct-2-enyl p-nitrophenyl ether.

Following the foregoing procedure, each of the p-nitrophenyl ethers under Column I is converted into the corresponding hydroxy substituted compound, for example, 7-hydroxy-3,7-dimethyloctyl p-nitrophenyl ether is obtained from 3,7-dimethyloct-6-enyl p-nitrophenyl ether.

EXAMPLE 2

A precooled (0°) solution of p-nitrophenyl geranyl ether (826 mg.; 3 millimol) in absolute ethanol (10 ml.) is treated under stirring with a solution of mercuric acetate (1.05 g.) in absolute ethanol (20 ml.). After 30 minutes, the mixture is treated with 3M—NaOH (3 ml.) and a solution of sodium borohydride (62.7 mg.) in 3M—NaOH (3 ml.). The stirring is continued for additional 1 hour, the mixture diluted with water and extracted with petroleum ether. The extract is washed with water, dried over magnesium sulfate and evaporated to afford a crude residue which contained the starting p-nitrophenyl geranyl ether in addition to the required product. Purification is performed on a column of silica gel (100 g.) in the solvent mixture petroleum ether-ether (9:1) to yield 7-ethoxy-3,7-dimethyloct-2-enyl p-nitrophenyl ether.

EXAMPLE 3

A solution of mercuric trifluoroacetate (1.4 g.) in absolute isopropyl alcohol (10 ml.) is added under stirring to a precooled solution of p-nitrophenyl geranyl ether (826 mg.) in absolute isopropyl alcohol (10 ml.). After 30 minutes, the mixture is treated with 3M—NaOH (3 ml.) and a solution of sodium borohydride (630 mg.) in 3M—NaOH (3 ml.). After 1 hour, the reaction mixture is diluted with water and extracted with petroleum ether. The extract is washed with water, dried over magnesium sulfate and evaporated to afford a crude residue containing the starting p-nitrophenyl geranyl ether in addition to the required product. The purification is performed on silica gel (100 g.) in the solvent mixture tetroleum ether-ether (9:1) to yield 7-ethoxy-3,7-dimethyloct-2-enyl p-nitrophenyl ether.

EXAMPLE 4

The process of Example 2 is repeated using each of the nitrophenyl ethers under Column I to yield 7-ethoxy-3,7-dimethyloctyl p-nitrophenyl ether, 7-ethoxy-1,5-dimethylhexyl p-nitrophenyl ether, 7-ethoxy-3,7-dimethylnon-2-enyl p-nitrophenyl ether, 7-ethoxy-3-ethyl-7-methylnon-2-enyl p-nitrophenyl ether and 8-ethoxy-4,8-dimethylnon-3-enyl p-nitrophenyl ether.

EXAMPLE 5

The process of Example 2 is repeated with the exception of using each of methanol, benzyl alcohol, isopropyl alcohol and n-hexanol in place of ethanol to yield 7-methoxy-3,7-dimethyloct-2-enyl p-nitrophenyl ether, 7-benzyloxy-3,7-dimethyloct-2-enyl p-nitrophenyl ether, 7-isopropoxy-3,7-dimethyloct-2-enyl p-nitrophenyl ether and 7-n-hexyloxy-3,7-dimethyloct-2-enyl p-nitrophenyl ether.

Similarly, the corresponding 7-methoxy, 7-benzyloxy, 7-isopropoxy and 7-n-hexyloxy derivatives of citronellyl p-nitrophenyl ether are obtained.

EXAMPLE 6

Following the procedure of Example 1(A), each of 3,4-dinitrophenol, 2,4-dinitrophenol, 2-chloro-4-nitrophenol, 2-bromo-4-nitrophenol, 4-chlorophenol, 2,4-dichlorophenol, 3,4-dichlorophenol, 2,3-dichlorophenol, 2,4,6-trichlorophenol and 2,4,5-trichlorophenol is alkylated using geranyl bromide and citronellyl bromide to yield the corresponding ethers.

By use of the process of Example 2, the addition of ethanol to the above ethers is accomplished to yield:

7-ethoxy-3,7-dimethyloct-2-enyl 3,4-dinitrophenyl ether,
7-ethoxy-3,7-dimethyloct-2-enyl 2,4-dinitrophenyl ether,
7-ethoxy-3,7-dimethyloct-2-enyl 2-chloro-4-nitrophenyl ether,
7-ethoxy-3,7-dimethyloct-2-enyl 2-bromo-4-nitrophenyl ether,
7-ethoxy-3,7-dimethyloct-2-enyl 4-chlorophenyl ether,
7-ethoxy-3,7-dimethyloct-2-enyl 2,4-dichlorophenyl ether,
7-ethoxy-3,7-dimethyloct-2-enyl 3,4-dichlorophenyl ether,
7-ethoxy-3,7-dimethyloct-2-enyl 2,3-dichlorophenyl ether,
7-ethoxy-3,7-dimethyloct-2-enyl 2,4,6-trichlorophenyl ether,
7-ethoxy-3,7-dimethyloct-2-enyl 2,4,5-trichlorophenyl ether and the corresponding 7-ethoxy-3,7-dimethyloctyl substituted phenyl ethers.

EXAMPLE 7

To a solution of 2 g. of sodium in 50 ml. of methanol at about 0° is added about 35 g. of p-nitrophenyl mercaptan. After about 0.5 hour, about 15 g. of 3,7-dimethyloct-6-enyl bromide is added and then the mixture refluxed for about 3 hours. Then the solvent is evaporated and the concentrate taken up in petroleum ether which is washed with water, dried over magnesium sulfate and evaporated to yield 3,7-dimethyloct-6-enyl p-nitrophenyl sulfide which is used as the starting material in the process of Example 2 to yield 7-ethoxy-3,7-dimethyloctyl p-nitrophenyl sulfide.

EXAMPLE 8

To 210 ml. of a 0.5M solution of sodium metaperiodate (aqueous methanol 1:1) at 0° is added 0.1 mol of 7-ethoxy-3,7-dimethyloctyl p-nitrophenyl sulfide. The mixture is stirred at 0° for 4 hours and then filtered to remove precipitated sodium iodate. The filtrate is diluted with water and then extracted with chloroform. The extract is dried over magnesium sulfate and solvent removed by evaporation to yield 7-ethoxy-3,7-dimethyloctyl p-nitrophenyl sulfoxide.

EXAMPLE 9

To 200 ml. of aqueous methanol (1:1) containing 0.2 moles of sodium metaperiodate is added 0.1 mol of 7-ethoxy-3,7-dimethyloctyl p-nitrophenyl sulfide. The mixture is maintained at about 30° for 6 hours. After cooling, the mixture is filtered to remove precipitated sodium iodate. The filtrate is diluted with water and then extracted with chloroform. The extract is dried over magnesium sulfate and solvent removed by evaporation to yield 7-ethoxy-3,7-dimethyloctyl p-nitrophenyl sulfone.

EXAMPLE 10

Following the procedure of Example 1(A), each of 2,3,4-trichlorophenol, 2,4-dichloro-6-nitrophenol, 2,5-dichloro-4-nitrophenol, 2,6-dichloro-4-nitrophenol and 2,6-diiodo-4-nitrophenol is alkylated using geranyl bromide and citronellyl bromide to yield the corresponding ethers.

By use of the process of Example 2, the addition of ethanol to the thus-prepared ethers is accomplished to prepare:

7-ethoxy-3,7-dimethyloct-2-enyl 2,3,4-trichlorophenyl ether, 7-ethoxy-3,7-dimethyloct-2-enyl 2,4-dichloro-6-nitrophenyl ether, 7-ethoxy-3,7-dimethyloct-2-enyl 2,5-dichloro-4-nitrophenyl ether, 7-ethoxy-3,7-dimethyloct-2-enyl 2,6-dichloro-4-nitrophenyl ether, 7-ethoxy-3,7-dimethyloct-2-enyl 2,6-diiodo-4-nitrophenyl ether and the respective 7-ethoxy-3,7-dimethyloctyl substituted phenyl ethers.

Juvenile hormone activity of the compounds of the present invention is demonstrated on last instar larvae of Dysdercus cingulatus and Graphasoma italicum and freshly molted pupae of Tenebrio molitor by topical application of 7-ethoxy-3,7-dimethyloct-2-enyl p-nitrophenyl ether in acetone. The ID-50 activity unit, in micrograms, is 0.08 for Dysdercus cingulatus, 0.5 for Graphasoma italicum and 0.005 for Tenebrio molitor. In larger amounts, the compounds of the present invention cause sterility of adult females, especially with Hemipterans.

We claim:

1. A compound selected from those of formulas I and II:

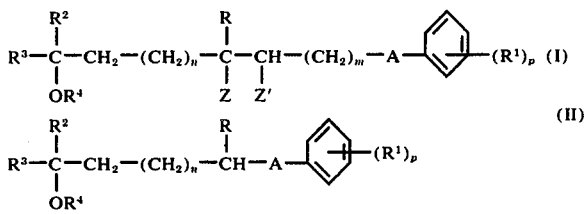

wherein, A is oxygen, $R^1$ is nitro or halo; each of R, $R^2$ and $R^3$ is lower alkyl; $R^4$ is hydrogen, lower alkyl, cycloalkyl or aralkyl; m is the positive integer one or two; n is the positive integer two or three; p is zero or the positive integer one to five; and each of Z and Z' is hydrogen or together form a carbon-carbon bond.

2. A compound according to claim 1 wherein Z and Z' together form a carbon-carbon bond and $R^1$ is halo.

3. A compound according to claim 2 which is 7-ethoxy-3,7-dimethyloct-2-enyl-4-chlorophenyl ether.

4. A compound to claim 1 wherein each of R and $R^2$ is methyl and $R^3$ is methyl or ethyl.

5. A compound according to claim 4 wherein $R^4$ is hydrogen, methyl or ethyl.

6. A compound according to claim 1 of formula II wherein each of R, $R^2$ and $R^3$ is methyl or ethyl and n is two.

7. A compound according to claim 6 wherein each of R, $R^2$ and $R^3$ is methyl.

8. A compound according to claim 7 wherein $R^4$ is hydrogen, methyl or ethyl.

9. A compound according to claim 1 wherein each of Z and Z' is hydrogen.

10. A compound according to claim 5 wherein each of Z and Z' is hydrogen.

11. A compound according to claim 4 wherein p is two to five and $R^1$ is nitro and chloro.

12. A compound according to claim 4 wherein p is two to five and $r^1$ is nitro and bromo.

13. A compound according to claim 1 wherein p is one and $R^1$ is in the para position.

* * * * *